(12) United States Patent
Fu et al.

(10) Patent No.: US 8,709,446 B2
(45) Date of Patent: Apr. 29, 2014

(54) HYR1 AS A TARGET FOR ACTIVE AND PASSIVE IMMUNIZATION AGAINST CANDIDA

(75) Inventors: Yue Fu, Torrance, CA (US); Guanpingsheng Luo, Torrance, CA (US); Ashraf Ibrahim, Irvine, CA (US); Brad Spellberg, Rancho Palos Verdes, CA (US); John Edwards, Jr., Palos Verdes Estates, CA (US)

(73) Assignee: Los Angeles Biomedical Research Institute at Harbor—UCLA Medical Center, Torrance, CA (US)

( * ) Notice: Subject to any disclaimer, the term of this patent is extended or adjusted under 35 U.S.C. 154(b) by 0 days.

(21) Appl. No.: 13/382,088

(22) PCT Filed: Jul. 2, 2010

(86) PCT No.: PCT/US2010/040949
§ 371 (c)(1),
(2), (4) Date: May 29, 2012

(87) PCT Pub. No.: WO2011/003085
PCT Pub. Date: Jan. 6, 2011

(65) Prior Publication Data
US 2012/0237534 A1    Sep. 20, 2012

Related U.S. Application Data

(60) Provisional application No. 61/223,005, filed on Jul. 3, 2009.

(51) Int. Cl.
*A61K 39/00* (2006.01)
*A61K 38/00* (2006.01)
*C07K 1/00* (2006.01)

(52) U.S. Cl.
USPC .......... 424/274.1; 424/184.1; 424/185.1; 514/1.1; 530/350; 530/300; 530/824

(58) Field of Classification Search
None
See application file for complete search history.

(56) References Cited

U.S. PATENT DOCUMENTS

| | | | |
|---|---|---|---|
| 6,747,137 B1 * | 6/2004 | Weinstock et al. | ......... 536/23.1 |
| 7,241,613 B1 | 7/2007 | Willins et al. | |
| 2007/0027309 A1 | 2/2007 | Weinstock et al. | |

FOREIGN PATENT DOCUMENTS

WO    WO-2011003085 A1    1/2011

OTHER PUBLICATIONS

Greenspan et al. Nature Biotechnology 7: 936-937, 1999.*
Bailey et al., "The *Candida albicans* HYR1 Gene, Which is Activated in Response to Hyphal Development, Belongs to a Gene Family Encoding a Yeast Cell Wall Proteins," *J. Bacteriol.* 178:5353-5360 (1996).
Bates et al., "*Candida albicans* Iff11, a Secreted Protein Required for Cell Wall Structure and Virulence," *Infect. Immun.* 75:2922-2928 (2007).
Database Geneseq. "*C. albicans* Hyphally Regulated Protein, SEQ ID No. 326," retrieved from EBI Accession No. GSP:AJF41554 on Nov. 1, 2007.
Database Geneseq. "*Candida albicans* Protein, SEQ ID No. 15577," retrieved from EBI Accession No. GSP:ATC95389 on Oct. 30, 2008.
Ibrahim et al., "Vaccination with Recombinant N-Terminal Domain of Als1p Improves Survival During Murine Disseminated Candidiasis by Enhancing Cell-Mediated, Not Humoral, Immunity," *Infect. Immun.* 73:999-1005 (2005).
Luo et al., "Neutrophils Inhibit Candidal Expression of *HYR1*, Which Mediates Resistance to Neutrophil Killing," Abstract M-1583. 48th Annual Interscience Conference on Antimicrobial Agents and Chemotherapy / 46th Annual Meeting of ISDA, American Society for Microbiology. Washington, DC. vol. 48, p. 654, Jan. 1, 2008.
Luo et al., "*Candida albicans* Hyr1p Confers Resistance to Neutrophil Killing and is a Potential Vaccine Target," *J. Infect. Dis.* 201:1718-1728 (2010).
Uniprot Submission P46591. Nov. 1995. Retrieved from the internet Sep. 16, 2010. http://www.uniprot.org/uniprot/P46591.txt?version=39.
Zhang et al., "Crystal Structure of Glutathione-Dependent Phospholipid Peroxidase Hyr1 from the Yeast *Saccharomycas cerevisiae*," *Proteins* 73:1058-1062 (2008).
International Search Report for International Application No. PCT/US2010/040949, completed Oct. 8, 2010, mailed Jun. 6, 2011 (3 pages).
International Preliminary Report on Patentability for International Application No. PCT/US2010/040949, issued Jan. 4, 2012 (5 pages).
Written Opinion of the International Searching Authority for International Application No. PCT/US2010/040949, completed Oct. 8, 2010, mailed Jun. 6, 2011 (4 pages).
Supplementary European Search Report for European Patent Application No. 10794828.3, dated Dec. 18, 2012 (9 pages).
First Office Action for Chinese Patent Application No. 201080039446.5, issued May 31, 2013 (English Language Translation Provided) (11 Pages).
Examination Report for New Zealand Patent Application No. 597442, dated Jul. 18, 2012 (2 pages).
Second Office Action for Chinese Patent Application No. 201080039446.5, issued Nov. 18, 2013 (English language translation provided).

* cited by examiner

*Primary Examiner* — S. Devi
(74) *Attorney, Agent, or Firm* — Clark & Elbing LLP

(57) ABSTRACT

The invention features HYR1 as a vaccine target and as a prophylactic strategy for combating disseminated candidiasis.

10 Claims, 6 Drawing Sheets

HYR1 AS A TARGET FOR ACTIVE AND PASSIVE IMMUNIZATION AGAINST CANDIDA

CROSS-REFERENCE TO RELATED APPLICATIONS

This application is the U.S. National Stage filing under 35 U.S.C. §371 of International Application No. PCT/US2010/040949, filed Jul. 2, 2010, which claims the benefit of U.S. Provisional Patent Application No. 61/223,005, filed Jul. 3, 2009.

STATEMENT AS TO FEDERALLY FUNDED RESEARCH

This invention was made with government support under Public Health Service grants R21 AI066010, R01 AI067703, R01 AI063503, and R03 AI083251. The United States Government has certain rights in this invention.

FIELD OF INVENTION

This invention relates to Candida hyphal cell wall proteins, to antibodies resulting from an immune response to vaccination with Candida hyphal cell wall proteins and to methods for the prevention and/or treatment of candidiasis and other bacterial infections with Candida hyphal cell wall proteins.

BACKGROUND OF THE INVENTION

All documents referred to herein, or the indicated portions, are hereby incorporated by reference herein including U.S. Provisional Application Ser. No. 61/223,005, filed Jul. 3, 2009. No document, however, is admitted to be prior art to the claimed subject matter.

Approximately 60,000 cases of disseminated candidiasis occur per year in the United States [1], resulting in billions of dollars of health care expenditures. Given the 40% mortality rate of such infections, there is a need to identify new prophylactic or therapeutic targets for intervention.

The primary host defense mechanism against disseminated candidiasis is phagocytic killing of the organism [2, 3]. Only phagocytic cells are capable of directly killing Candida in vitro [4]. Additionally, within thirty-minutes of intravenous inoculation of Candida in mice, rabbits, dogs, or humans, yeasts are retained within the reticuloendothelial system, especially in the liver. The liver, rich in Kupffer macrophages, is capable of clearing 99.9% of yeast in the portal system during a single pass [5], underscoring the effectiveness of phagocytic defense mechanisms against the fungus. Hence, resistance of C. albicans to phagocyte killing is an important virulence function of the organism.

Cell surface glycosyl phosphatidylinositol (GPI)-anchored proteins are at the critical interface between pathogen and host, making these proteins likely participants in host-pathogen interactions [6].

The identification of effectors in the regulatory pathways of the organism that contribute to virulence offers the opportunity for therapeutic intervention with methods or compositions that are superior to existing antifungal agents. The identification of cell surface proteins or hyphal proteins that affect a regulatory pathway involved in virulence is particularly promising because characterization of the protein enables immunotherapeutic techniques that are likely superior to or synergistic with existing antifungal agents when fighting a candidal infection.

The virulence of C. albicans is regulated by several putative virulence factors of which adherence to host constituents and the ability to transform from yeast-to-hyphae are among the most critical in determining pathogenicity. While potent antifungal agents exist that are microbicidal for Candida, the attributable mortality of candidemia is approximately 38%, even with treatment with potent anti-fungal agents such as amphotericin B. Also, existing agents such as amphotericin B tend to exhibit undesirable toxicity. Although additional antifungals may be developed that are less toxic than amphotericin B, it is unlikely that agents will be developed that are more potent. Therefore, either passive or active immunotherapy to treat or prevent disseminated candidiasis is a promising alternative to standard antifungal therapy.

Thus, there exists a need for effective immunogens that will provide host immune protection and passive immunoprotection against Candida and other immunogenically related pathogens. The present invention satisfies this need and provides related advantages as well.

SUMMARY OF THE INVENTION

The present invention features Candida HYR1 polypeptide antigens, and the therapeutic uses of such antigens. The HYR1 polypeptide antigens of the present invention may be used to treat or prevent Candida infection in a subject.

By screening a novel conditional overexpression/suppression system focusing on GPI-anchored proteins in C. albicans, we identified HYR1 as a virulence factor. HYR1 is a hyphae co-expressed gene, the null mutant strain of which does not display any morphologic abnormality in vitro [7]. Below we provide results demonstrating that HYR1 mediates resistance to phagocytic killing in vitro, modulates tissue fungal burden in vivo, and is therefore a vaccine target to ameliorate the severity of disseminated candidiasis.

Definitions

By a "HYR1" polypeptide is meant a polypeptide that is substantially identical to the amino acid sequence of SEQ ID NO:1. Desirably, a HYR1 polypeptide has at least 70, 75%, 80%, 85%, 90%, 95%, 99%, or even 100% identity to the amino acid sequence of SEQ ID NO: 1.

By "fragment of a HYR1 polypeptide" or a "HYR1 fragment" is meant a fragment of a HYR1 polypeptide containing fewer than 937, 936, or 935 amino acids. Preferred HYR1 fragments are between 300 and 350 or 250 to 500 amino acids in length. Desirably, the fragment is fewer than 937, 936, 935, 934, 933, 932, 931, or 930, 920, 910, 900, 890, 880, 870, 860, 850, 840, 830, 820, 810, 800, 790, 780, 770, 760, 750, 740, 730, 720, 710, 700, 690, 680, 670, 660, 650, 640, 630, 620, 610, 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids, and desirably, is immunogenic. A HYR1 fragment, for example, may contain one or more conservative amino acid substitutions in the sequence of SEQ ID NO: 2. Additional desirable HYR1 fragments contain one or more conservative amino acid substitutions in the sequence of SEQ ID NO: 2 and/or at least one flanking amino acid (e.g., 1, 2, 3, 4, 5, 6, 7, 8, 9, or 10 flanking amino acids) at the N- and/or C-terminus of the sequence of SEQ ID NO: 2. Other preferred HYR1 fragments contain seven or more continuous amino acids of the sequence of SEQ ID NO: 2.

Non-limiting examples of a HYR1 fragment include amino acids 1-40, 10-50, 20-60, 30-70, 40-80, 50-90, 60-100, 70-110, 80-120, 90-130, 100-140, 110-150, 120-160, 130-170, 140-180, 150-190, 160-200, 170-210, 180-220, 190-230, 200-240, 210-250, 220-260, 230-270, 240-280, 250-290, and 260-300, 270-310, 280-320, and 290-331 amino acids of the sequence of SEQ ID NO: 2; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in the sequence of SEQ ID NO: 2; one or more amino acids (e.g., 1, 2, 3, 4, 5, 6, 7, 8, 9, 10, 11, 12, 13, 14, 15, or 16 amino acids) truncated from the N and/or C-terminus of the sequence of SEQ ID NO: 2; and at least one flanking amino acid (e.g., 1, 2, 3, 4, 5, 6, 7, 8, 9, or 10 flanking amino acids) at the N- and/or C-terminus of the sequence of SEQ ID NO: 2.

By "substantially identical" is meant a polypeptide exhibiting at least 50%, desirably 60%, 70%, 75%, or 80%, more desirably 85%, 90%, or 95%, and most desirably 99% amino acid sequence identity to a reference amino acid sequence. The length of comparison sequences will generally be at least 10 amino acids, desirably at least 15 contiguous amino acids, more desirably at least 20, 25, 50, 75, 90, 100, 150, 200, 250, 275, 300, 310, 315, 320, 325, 330, 335, 340, 345, or 350 contiguous amino acids, and most desirably the full-length amino acid sequence.

Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications. Multiple sequences may also be aligned using the Clustal W(1.4) program (produced by Julie D. Thompson and Toby Gibson of the European Molecular Biology Laboratory, Germany and Desmond Higgins of European Bioinformatics Institute, Cambridge, UK) by setting the pairwise alignment mode to "slow," the pairwise alignment parameters to include an open gap penalty of 10.0 and an extend gap penalty of 0.1, as well as setting the similarity matrix to "blosum." In addition, the multiple alignment parameters may include an open gap penalty of 10.0, an extend gap penalty of 0.1, as well as setting the similarity matrix to "blosum," the delay divergent to 40%, and the gap distance to 8.

By "conservative amino acid substitution," as used herein, is meant replacement, in an amino acid sequence, of an amino acid for another within a family of amino acids that are related in the chemical nature of their side chains.

Genetically encoded amino acids can be divided into four families: acidic (aspartate, glutamate); basic (lysine, arginine, histidine); nonpolar (alanine, valine, leucine, isoleucine, proline, phenylalanine, methionine, tryptophan); and uncharged polar (glycine, asparagine, glutamine, cysteine, serine, threonine, tyrosine). Phenylalanine, tryptophan, and tyrosine are sometimes grouped as aromatic amino acids. In similar fashion, the amino acids can also be separated into the following groups: acidic (aspartate, glutamate); basic (lysine, arginine, histidine); aliphatic (glycine, alanine, valine, leucine, isoleucine, serine, threonine), with serine and threonine optionally grouped separately as aliphatic-hydroxyl; aromatic (phenylalanine, tyrosine, tryptophan); amide (asparagine, glutamine); and sulfur-containing (cysteine, methionine).

Whether a change in the amino acid sequence results in a functional homolog can be determined by assessing the ability of the variant peptide to function in a fashion similar to the wild-type protein using standard methods such as the assays described herein.

Desirable embodiments of the invention, include at least one conservative amino acid substitution in the amino acid sequence of SEQ ID NO: 1 or 2; and more desirably 1, 2, 3, 4, 5, 6, 7, 8, 9, or 10 conservative amino acid substitutions in the sequence of SEQ ID NO: 1 or 2.

By "flanking amino acid" is meant an amino acid in a polypeptide sequence that is immediately adjacent to the N- or C-terminus of a particular defined sequence. Desirably, a flanking amino acid is present on the N- and/or C-terminus of the amino acid sequence of SEQ ID NO: 1 or 2 or a fragment thereof; and more desirably, 1, 2, 3, 4, 5, 6, 7, 8, 9, or 10 flanking amino acids are present at the N- and/or C-terminus of the amino acid sequence of SEQ ID NO: 1 or 2, or fragment thereof.

As used herein "fusion protein" refers to a polypeptide consisting of (1) a HYR1 polypeptide, HYR1 fragment; and (2) a fusion partner.

As used herein "fusion partner" refers to a heterologous sequence that can be fused to a HYR1 polypeptide or HYR1 fragment. Examples of fusion partners are described herein and include detection markers, stabilizing domains, or sequences which aid in production or purification of the protein.

As used herein "immune response" refers to the activation of an organism's immune system in response to an antigen or infectious agent. In vertebrates, this may include, but is not limited to, one or more of the following: naïve B cell maturation into memory B cells; antibody production by plasma cells (effector B cells); induction of cell-mediated immunity; activation and cytokine release by $CD4^+$ T cells; activation and cytokine release of $CD8^+$ T cells; cytokine recruitment and activation of phagocytic cells (e.g., macrophages, neutrophils, eosinophils); and/or complement activation.

By "immunogenic" is meant any substance that is capable of inducing an immune response in a subject.

By "pharmaceutically acceptable salt" is meant any non-toxic acid addition salt or metal complex used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid, phosphoric acid, or the like. Metal complexes include zinc, iron, and the like.

By "pharmaceutically acceptable carrier" is meant any solution used to solubilize and deliver an agent to a subject. A desirable pharmaceutically acceptable carrier is saline. In desirable embodiments, a pharmaceutically acceptable carrier includes an adjuvant. Exemplary adjuvants are described herein. Other physiologically acceptable carriers and their formulations are known to one skilled in the art and described, for example, in Remington's Pharmaceutical Sciences, (20th edition), ed. A. Gennaro, 2003, Lippincott Williams & Wilkins.

By "isolated" is meant a protein (or a fragment thereof) that has been separated from components that naturally accompany it. Typically, the polypeptide is substantially isolated when it is at least 60%, by weight, free from the proteins and naturally occurring organic molecules with which it is naturally associated. The definition also extends to a polypeptide separated from its flanking amino acids (e.g., for an amino acid sequence, isolated refers to a sequence that is free from the flanking amino acids with which the sequence is naturally associated in a polypeptide). Preferably, the polypeptide is at least 75%, more preferably at least 90%, and most preferably at least 99%, by weight, isolated. An isolated polypeptide may be obtained by standard techniques, for example, by extraction from a natural source (e.g., purification from a cell infected with Candida), by expression of a recombinant nucleic acid encoding a HYR1 fragment; or fusion protein thereof, by chemically synthesizing the polypeptide. Purity can be measured by any appropriate method, e.g., by column chromatography, polyacrylamide gel electrophoresis, or HPLC analysis.

By a "therapeutically effective amount" is meant the amount of a immunogenic compound (e.g., polypeptide, fragment, fusion protein, or vaccine) required to generate in a subject one or more of the following effects: an immune response; a decrease in the level of Candida infection (e.g., a reduction of at least 5%, 10%, 20%, or 30%; more desirably 40%, 50%, 60%, or 70%; and most desirably 80% or 90%); a decrease (e.g., at least a 10%, 20%, 30%, 40%, 50%, 60%, 70%, 80%, 90%, or even 100% reduction) in one or more symptoms of Candida infection in a patient; or increased resistance to a new Candida infection (e.g., an increase of at least 5%, 10%, 20%, 30%, 40%, or 50%; more desirably 60%, 70%, 80%, or 90%; or most desirably 100%, 200%, or 300%).

Other features and advantages of the invention will be apparent from the following Detailed Description, the drawings, and the claims.

DETAILED DESCRIPTION

Figure 1:
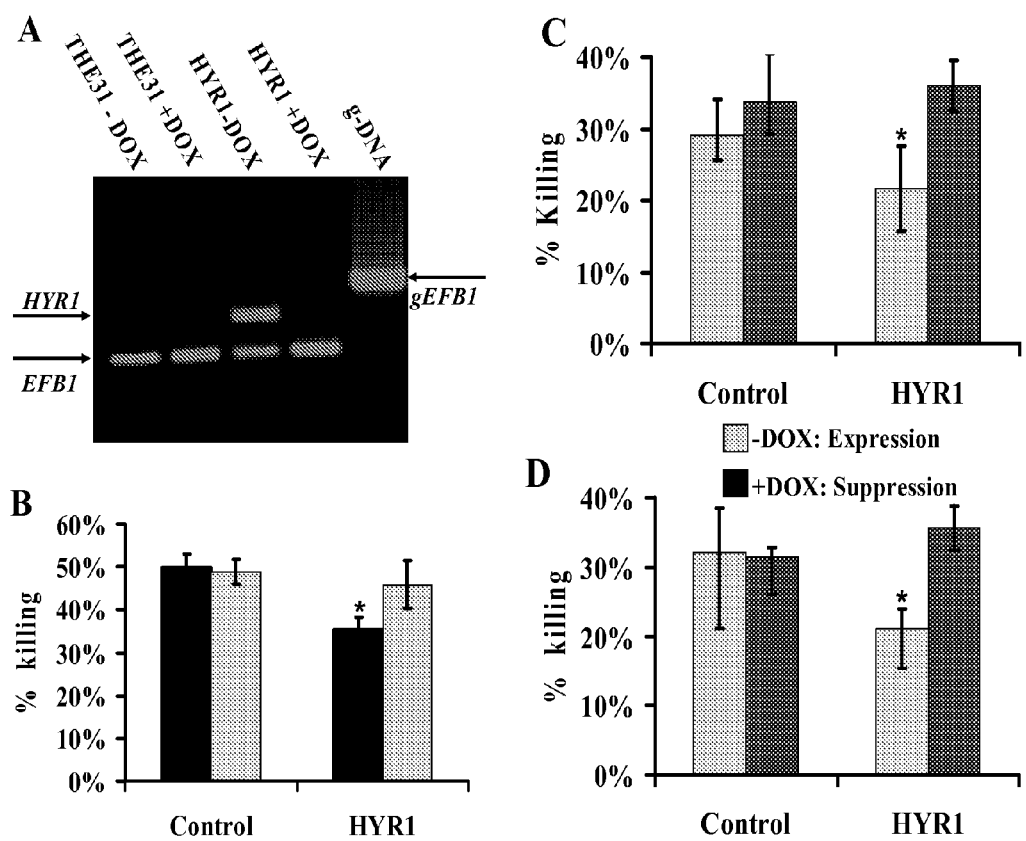
FIG. 1. Conditional expression of HYR1 enhanced neutrophil and macrophage mediated killing of C. albicans. (A) Confirmation of HYR1 conditional overexpression/suppression strain CAAH-31. RT-PCR results of HYR1 demonstrating overexpression of the gene in −DOX medium and lack of expression in +DOX medium. EFB1 fragment was co-amplified and served as a control. Lack of genomic DNA contamination in cDNA preparations was demonstrated by the absence of 919 bp band containing the intron of EFB1. THE31 was the wild-type control strain. (B) C. albicans strains were grown in YPD with DOX (suppression of HYR1) and without DOX (overexpression of HYR1) at 30° C. overnight and then cocultured with human neutrophil; (C)C. albicans cocultured with HL-60 derived neutrophil; (D) with HL-60 derived macrophage.

Candida albicans is a common pathogen in humans. For example, C. albicans, while normally a harmless commensal, can cause a variety of conditions ranging from superficial mucocutaneous infection such as vaginal and/or oropharyngeal candidiasis, to deep organ involvement in disseminated candidiasis. Prior to causing disease, the fungus colonizes the gastrointestinal tract, and in some cases skin and mucous membranes. Adherence to host mucosal surfaces is a key prerequisite for this initial step. After colonization, C. albicans enters the bloodstream via infected intravascular devices or by transmigration through gastrointestinal mucosa compromised by chemotherapy or stress ulcerations. Organisms then disseminate via the bloodstream, bind to and penetrate the vascular endothelium to egress from the vascular tree, and invade deep organs such as liver, spleen, and kidney.

The identification and functional characterizations of a HYR1 fragment described herein allows this polypeptide to be effectively utilized in the treatment of candidiasis.

The nature of the pathogenesis of *C. albicans* by adherence to endothelial cells is discussed in U.S. Pat. No. 5,578,309 which is specifically incorporated herein by reference in its entirety. For a description of an HYR1 gene and characteristics thereof, including the characterization of the gene product see, Bailey et al. (*Journal of Bacteriology* 178:5353-5360, 1996).

The invention provides a vaccine having an isolated HYR1 fragment, and optionally an adjuvant in a pharmaceutically acceptable medium. The vaccine can be an HYR1 fragment derived from a *Candida* species such as *Candida albicans, Candida krusei, Candida tropicalis, Candida glabrata*, or *Candida parapsilosis*.

The invention utilizes the gene product of *C. albicans* HYR1 sequence as a vaccine to treat, prevent, or alleviate disseminated candidiasis. The vaccine is effective against different strains of *C. albicans* as well as against different *Candida* species.

Thus, according to one aspect, the invention provides an HYR1 fragment useful when formulated in a pharmaceutical composition and administered as a vaccine with or without an adjuvant. An HYR1 fragment can be of candidal origin and can be obtainable, for example, from species belonging to the genera *Candida*, for example *Candida parapsilosis, Candida krusei, Candida glabrata*, and *Candida tropicalis*. An HYR1 fragment can be obtained in isolated or purified form, and thus, according to one embodiment of the invention an HYR1 fragment is formulated as a vaccine to cause an immune response in a patient to elicit an immune response against *Candida*.

The invention also provides a method of treating or preventing disseminated candidiasis. The method includes administering an immunogenic amount of a vaccine of an HYR1 fragment. The vaccine can be administered with or without an adjuvant. The HYR1 fragment can be derived from different *Candida* strains as well as from different *Candida* species such as *Candida albicans, Candida krusei, Candida tropicalis, Candida glabrata*, and *Candida parapsilosis*.

The effectiveness of the vaccines of the invention against different *Candida* strains, different *Candida* species, other bacteria and infectious agents and their wide range of immune activity are assessed according to standard methods such as those described further below.

Given the teachings and guidance provided herein, those skilled in the art will understand that immunotherapeutic methods well know in the art can be employed with one or more HYR1 fragments in a pharmaceutically acceptable composition administered as a vaccine with or without an adjuvant. For the purposes of this invention, the terms "pharmaceutical" or "pharmaceutically acceptable" refer to compositions formulated by known techniques to be non-toxic and, when desired, used with carriers or additives that can be safely administered to humans. Administration can be performed using well known routes including, for example, intravenous, intramuscular, intraperitoneal or sub-cutaneous injection. Such vaccines of the inventions also can include buffers, salts or other solvents known to these skilled in the art to preserve the activity of the vaccine in solution. Similarly, any of a wide range of adjuvants well known in the art can be employed with the vaccine of the invention to elicit, promote or enhance a therapeutically effective immune response capable of reducing or blocking binding, invasion and/or infection of *Candida* to a susceptible host cell.

It is understood that modifications which do not substantially affect the activity of the various embodiments of this invention are also included within the definition of the invention provided herein. Accordingly, the following examples are intended to illustrate but not limit the present invention.

Example I

*Candida albicans* Hyr1p Confers Resistance to Neutrophil Killing and is a Vaccine Target As is discussed above, *Candida albicans* is the most common cause of invasive fungal infections in humans. It is unclear how *C. albicans* escapes from phagocytic attack and survives in the hostile blood environment during life-threatening systemic infections. Using a conditional overexpression/suppression genetic strategy, we discovered that the HYR1 gene reduced phagocytic killing of *C. albicans* in vitro and increased tissue fungal burden in vivo. Concordant with its positive regulation by the transcription factor Bcr1p, HYR1 complemented the hyper-susceptibility to phagocyte-mediated killing of a bcr1 null mutant of *C. albicans* in vitro. Furthermore, heterologous expression of HYR1 in *Candida glabrata* rendered the organism more resistant to neutrophil killing. Finally, vaccination with recombinant Hyr1p significantly protected mice against hematogenously disseminated candidiasis. Thus, Hyr1 is an important virulence factor for *C. albicans*, mediating resistance to phagocyte killing. Hyr1p is accordingly a target for vaccine or other immunological or small molecule intervention to improve the outcomes of disseminated candidiasis.

Results

Conditional Expression of HYR1 in Blastospores Significantly Enhanced *C. albicans* Resistance to Phagocyte-Mediated Killing In Vitro To study the function of HYR1, we constructed a conditional overexpression/suppression strain of *C. albicans*, CAAH-31. In CAAH-31, one allele of HYR1 was controlled by the tetracycline regulated (TR)-promoter and the other allele was disrupted. By semi-quantitative RT-PCR, we confirmed that HYR1 was abundantly expressed when blastospores of CAAH-31 were grown in media without DOX, and was not detected in the presence of DOX (FIG. 1A). As expected, HYR1 was not detected in wild-type (THE31) blastospores because HYR1 is a hyphal co-expressed gene (FIG. 1A).

The HYR1 conditional overexpression strain, CAAH-31, and THE31 wild-type control had identical growth rates, irrespective of the presence or absence of DOX (doubling time for wild-type control strain without DOX=1.51±0.29 hr and with DOX=1.51±0.38 hr; doubling time for CAAH-31 strain without DOX=1.39±0.30 hr and with DOX=1.35±0.19 hr). We also evaluated the impact of HYR1 overexpression on the normal accumulation of other GPI-anchored proteins on the cell surface. By direct immunofluorescence, we confirmed that HYR1 overexpression had no impact on the accumulation of the GPI-anchored protein Als1p (data not shown) [8].

During routine screening for virulence-associated phenotypes, we determined the impact of conditional overexpression of HYR1 on candidal killing by human phagocytes. HYR1-expressing *C. albicans* (CAAH-31–DOX) was significantly more resistant to human neutrophil-mediated killing than wild-type *C. albicans* (which does not express HYR1 in the blastospore phase) and HYR1-suppressed *C. albicans*

(CAAII-31+DOX) (FIG. 1B). This phenotype was not due to DOX, as killing was not significantly different between the wild-type control and HYR1-suppressed *C. albicans* (+DOX).

We also performed candidal killing assays using the HL-60 cell line, which can be differentiated into either neutrophil-like or macrophage-like cells [9, 10]. Like freshly harvested human neutrophils, conditional overexpression of HYR1 reduced killing of *C. albicans* blastospores by both HL-60 neutrophil-like (FIG. 1C) and macrophage-like (FIG. 1D) cells in vitro.

Figure 2:
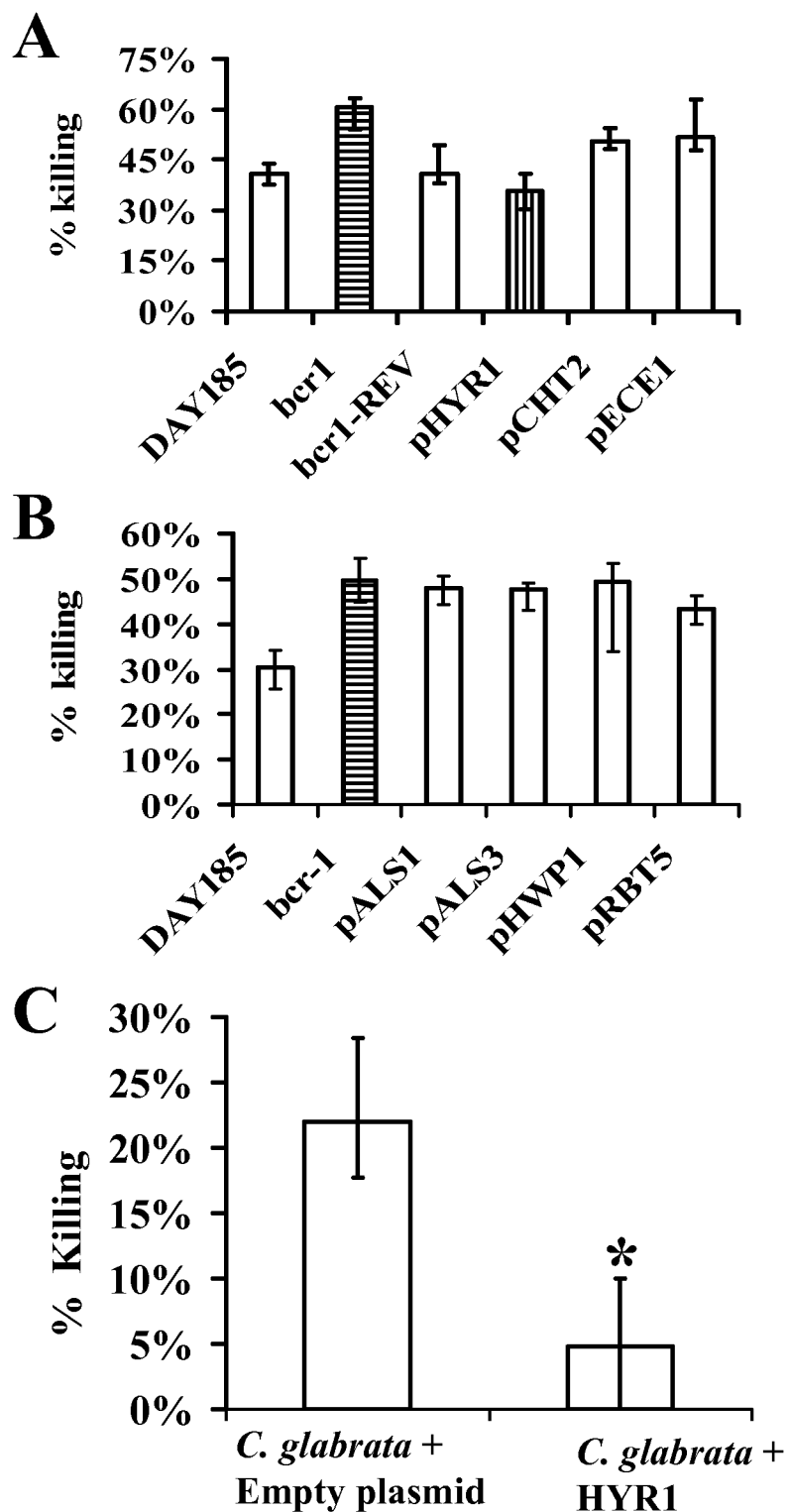
FIG. 2. Expression of Candida albicans HYR1 increased human neutrophil killing resistance in bcr1 null mutant or C. glabrata strain. (A and B) Autonomously expression of HYR1 in a bcr1 deficient strain of C. albicans completely complemented the hypersusceptibility of the parent strain to neutrophil killing resistance. C. albicans strains DAY185 (wild-type), $CJN_7O_2$ (bcr1 null mutant) and CJN698 (BCR1 complemented) CJN114, CJN1153, CJN1222, CJN1259, CJN1276, CJN1281, and CJN1288 (autonomously expressing ALS1, ALS3, HWP1, HYR1, RBT5, CHT2 and ECE1 in a bcr1 null mutant background, respectively) were grown in YPD overnight at 30° C. Data are displayed as median±interquartile. *P<0.04 vs. the wild-type and BCR1-complemented. (C) Heterologous expression of C. albicans HYR1 gene increased C. glabrata resistance to HL-60 derived neutrophil mediated killing. *P<0.0001.

Hyper-Susceptibility to Neutrophil Killing of bcr1 Null Mutant *C. albicans* was Complemented by HYR1 Expression In Vitro Since HYR1 is a downstream gene of the positive transcription regulator Bcr1p [17], we hypothesized that disruption of bcr1 would exacerbate susceptibility to neutrophil killing under conditions promoting wild-type *C. albicans* to express HYR1 (i.e. during hyphal formation). We therefore induced *C. albicans* to form germ tubes by incubating the cells in RPMI plus 10% FBS at 37° C. for 40 min. This condition is known to induce expression of HYR1 [18], and resulted in germ tubes short enough such that extensive hyphae were not formed, thereby enabling quantification of colony forming units (CFUs) in our kill assay. We compared neutrophil killing of the bcr1 null mutant strain ($CJN_7O_2$), a BCR1 complemented strain in the bcr1 null mutant background (CJN698), and a wild-type *C. albicans* strain (DAY185). The bcr1 null mutant was hyper-susceptible to neutrophil-mediated killing compared to the BCR1-complemented and wild-type control strains (FIG. 2A). Furthermore, the hyper-susceptibility to killing of bcr1-deficient *C. albicans* was fully complemented by autonomous expression of HYR1 in the bcr1 mutant background, but not by other cell surface encoding genes regulated by Bcr1p [17] (FIGS. 2A and 2B).

Resistance of *C. albicans* Overexpressing HYR1 to Phagocyte Killing can be Recapitulated by Heterologous Expression of HYR1 in *C. glabrata*

To further define the virulence phenotype mediated by HYR1, we expressed the gene heterologously in *C. glabrata* BG14 [19] using a plasmid pGRB2.2 carrying a constitutive PGK1 promoter [11]. We also generated a *C. glabrata* BG14 transformed with the empty plasmid, as a negative control. Expression of HYR1 in *C. glabrata* resulted in a 75% reduction in killing by HL-60-derived neutrophils in vitro, compared to the *C. glabrata* transformed with an empty plasmid (FIG. 2C).

Neutrophils Inhibit Candidal HYR1 Expression

Figure 3:
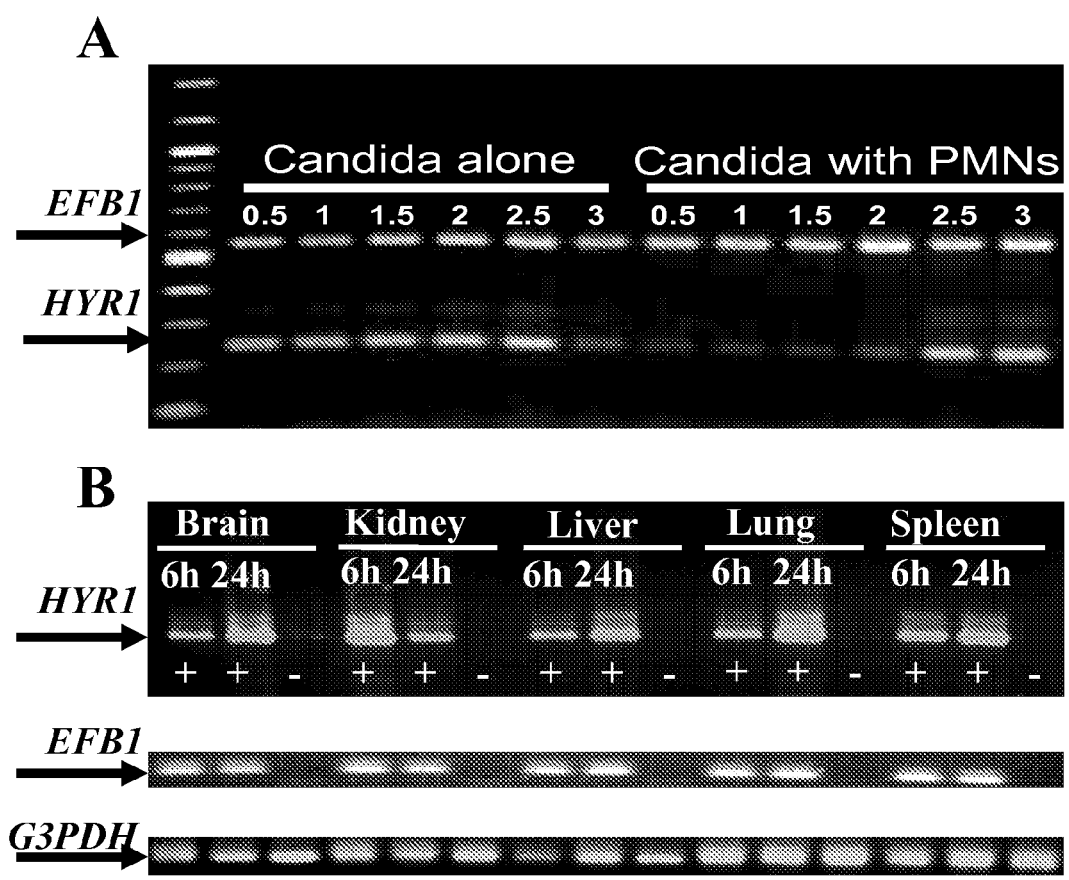
FIG. 3. Detection of HYR1 expression during disseminated candidiasis although its expression was initially inhibited by neutrophil in vitro. (A) Kidneys livers, lungs, spleens and brains were harvested 6 or 24 h after intravenous infection with C. albicans. Nested RT-PCR was used to detect expression of HYR1. C. albicans EFB1 and mouse house-keeping gene G3PDH were used as a control. + denotes infected mice, while − denotes uninfected mice. (B) HL-60 derived neutrophil inhibited C. albicans HYR1 expression. Wild-type C. albicans was cultured in RPMI 1640 plus 10% pooled human serum. Without neutrophil, HYR1 expression was detected after half hour induction. With neutrophil, HYR1 expression was inhibited two hours.

Because conditional overexpression of HYR1 conferred *Candida* resistance to neutrophil-mediated killing, we used RT-PCR to study the expression of wild-type *C. albicans* (SC5314) HYR1 in response to HL-60-derived neutrophils in vitro. HYR1 was expressed as early as 30 min after exposure to medium containing serum, and maintained high expression for 2.5 hr during culture (FIG. 3A). However, when *C. albicans* was exposed to HL-60-derived neutrophils in culture, even in the presence of serum, HYR1 expression was inhibited for up to 2 hr into the co-culture (FIG. 3A).

Wild-Type *C. albicans* Expresses HYR1 During Hematogenously Disseminated Candidiasis, Resulting in Increased Tissue Fungal Burden in Organs Rich in Phagocytes To determine whether HYR1 was expressed during hematogenously disseminated candidiasis, five major organs—brain, liver, lung, spleen and kidney—were harvested from mice infected with *C. albicans* wild-type strain after 6 and 24 hr of infection. An improved nested-RT-PCR assay [20] was used to assess HYR1 expression in vivo. HYR1 expression was detected in all five organs (FIG. 3B).

Figure 4:
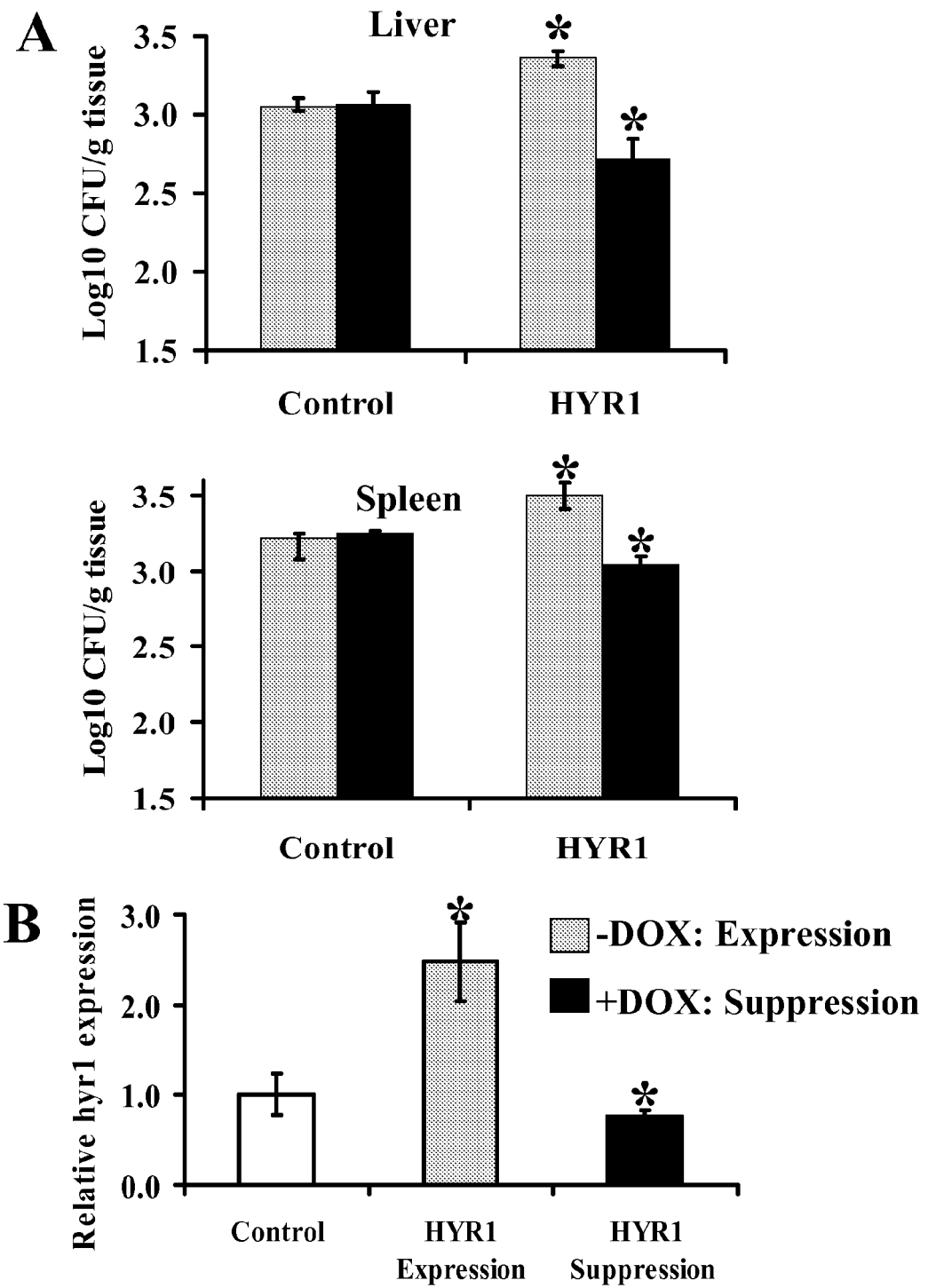
FIG. 4. HYR1 in vivo expression and its effect on fungal burden. To detect HYR1 expression during disseminated candidiasis, kidneys livers, lungs, spleens and brains were harvested 6 or 24 h after intravenous infection with C. albicans. Nested RT-PCR was used to detect expression of HYR1. C. albicans EFB1 and mouse house-keeping gene G3PDH were used as a control. + denotes infected mice, while − denotes uninfected mice (A). Conditional expression HYR1 increased fungal burden in organs with extensive tissue phagocytes. Burden of C. albicans in livers and spleens of immunocompetent mice (n=8 per group) infected with C. albicans HYR1 or control strain grown in conditional expressing (−DOX) or suppressing (+DOX) conditions (A) and the in vivo HYR1 expression (B). Livers and spleens were harvested one day post infection. The y-axes reflect lower limits of detection of the assay. Data are displayed as median±interquartile. *P<0.0001 vs. no expression of HYR1 strain (HYR1-DOX) or control strain.

Overexpression of HYR1 increased and suppression of HYR1 decreased fungal burden in the liver and spleen (FIG. 4A). Furthermore, we confirmed that the overexpressing strain had significantly higher levels of HYR1 than the wild-type strain in livers; the suppressed strain demonstrated a trend towards reduced levels (FIG. 4B). In contrast, HYR1 expression did not significantly alter fungal burden in the kidney (data not shown), an organ lacking resident phagocytes.

rHyr1p-N as a Vaccine Candidate

Figure 5:
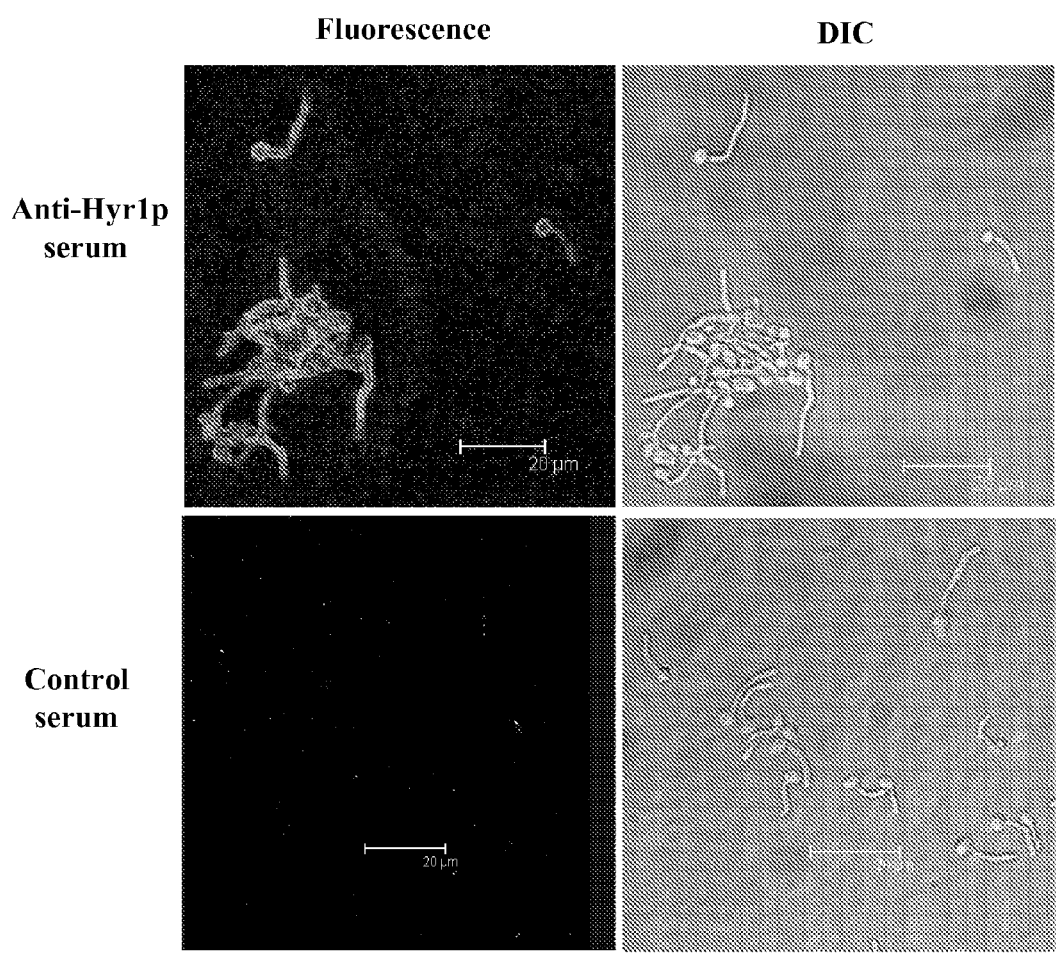
FIG. 5. Indirect immunofluorescence with anti-Hyr1p serum demonstrates surface expression of Hyr1p on C. albicans hyphae. Hyphal formation was induced by incubating C. albicans in RPMI 1640 for 90 min. Cells were stained with either the hyr1 null mutant pre-absorbed anti-Hyr1p serum (1:100) or the anti-protein preparation from the empty plasmid clone serum (negative control), followed by staining with ALEXA labeled anti-mouse Ab.

Based on sequence analysis, Hyr1p is predicted to be a cell surface protein [7]. To confirm this, we generated a recombinant N-terminal Hyr1p in *E. coli* transformed with an expression clone that includes amino acids 25-350 of the coding sequence (rHyr1p-N). Serum from mice immunized with rHyr1p-N was pre-absorbed against the hyr1 null mutant of *C. albicans* [7], followed by indirect immuno-staining on wild-type hyphae. We found that the cell wall of wild-type *C. albicans* hyphae was heavily stained (FIG. 5), confirming that it is cell-surface expressed, and hence exposed to the immune system.

Because Hyr1p is as a cell surface protein, which confers resistant to candidal killing by phagocytes, we sought to determine its potential as a vaccine candidate. Mice were vaccinated with rHyr1p-N plus adjuvant or adjuvant alone. Two weeks after the boost, mice were infected via the tail vein with highly virulent *C. albicans* SC5314. Vaccination with rHyr1p-N markedly improved survival of mice compared to those vaccinated with adjuvant alone (62.5 and 0% survival at 35 days, respectively) (FIG. 6A).

Figure 6:
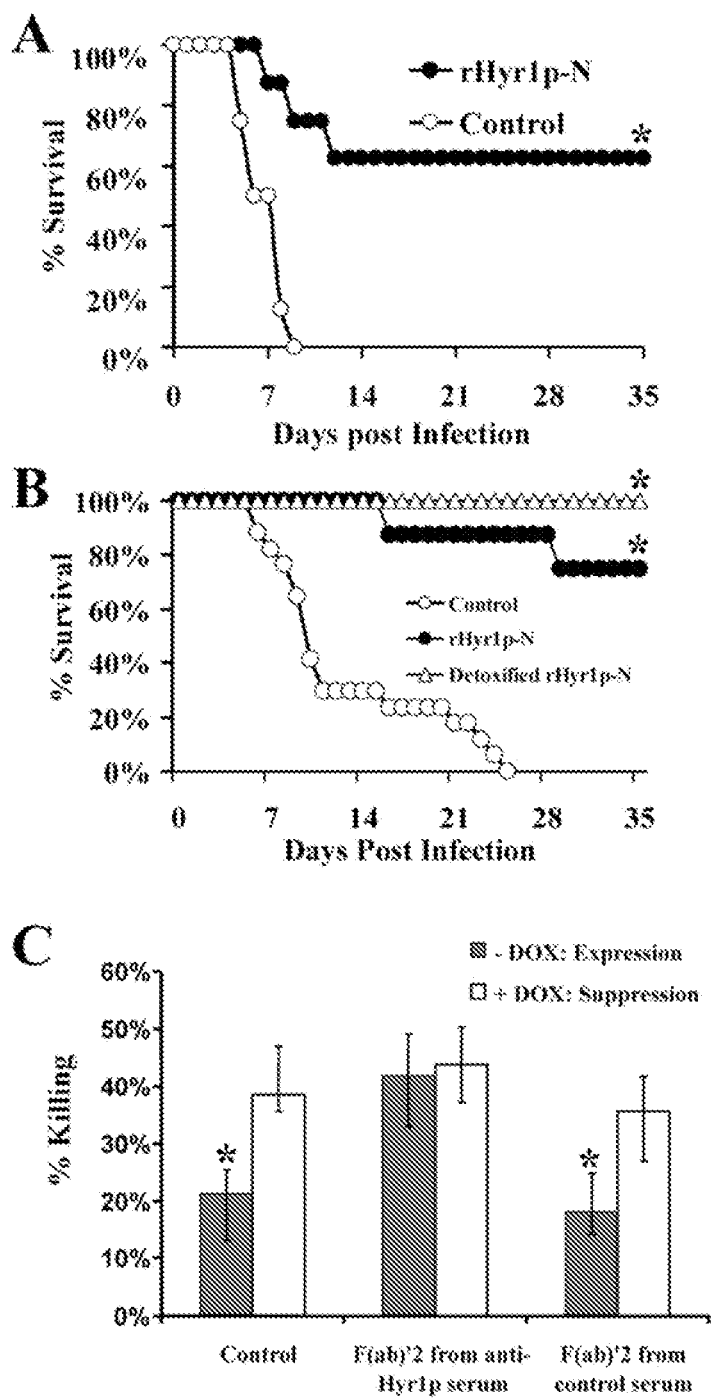
FIG. 6. Recombinant N-terminus of Hyr1p (rHyr1p-N) remarkably protected against murine hematogenously disseminated candidiasis. (A) Survival of mice (8 mice per group) vaccinated with rHyr1p-N mixed with complete or incomplete Freund's adjuvant and infected by means of the tail vein with $2.2 \times 10^5$ blastospores of Candida albicans SC5314. (B) Survival of mice (8 mice per group, except the control group, which had 17 mice) vaccinated with rHyr1p-N or detoxified rHyr1p-N mixed with 0.1% ALHYDROGEL and infected with $7 \times 10^5$ blastopsores of Candida albicans 15563. *P=0.001 by log-rank test. (C) Effect of vaccinated or control $F(ab)'_2$ on blocking mouse neutrophil killing of C. albicans conditionally expressed or suppressed Hyr1. Control denotes assay performed in the absence of either $F(ab)'_2$. Data are displayed as median±interquartile range. *P=0.001 by Mann-Whitney test.

Vaccination with rHyr1p-N mixed with complete or incomplete Freund's adjuvant or alum markedly improved survival of mice compared with those vaccinated with either adjuvant alone (FIGS. 6A and 6B).

Anti-rHyr1p Serum Enhanced Neutrophil Killing in Mice by Directly Inhibiting Hyr1p Neutrophil Resistance Function.

The protective effect of the rHyr1p-N vaccine suggested that the anti-rHyr1p serum might be able to neutralize the protective function of Hyr1p in *C. albicans*. To determine whether anti-rHyr1p antibodies could directly inhibit Hyr1p function, we isolated and prepared F(ab)'$_2$ fragments from total IgG of mice immunized with either rHyr1p-N or the control (preparation produced from *E. coli* cells transformed with the empty plasmid). We found that F(ab)'$_2$ from immune but not control serum was able to restore neutrophil killing of the HYR1 conditional expressing strain to levels equivalent to that of the suppressing strain (FIG. 6C).

Summary

In this study, we demonstrated that HYR1, a hyphal co-expressed gene [7, 21], encodes a candidal phagocyte resistance factor. Conditional expression of HYR1 in *Candida* blastospores caused the fungus to be more resistant to killing by phagocytes compared to wild-type *C. albicans* blastospores. Additionally, the function of HYR1 in *C. albicans* was recapitulated by heterologously expressing the gene in *C. glabrata* in vitro. We also found that a strain deficient in Bcr1p, a transcription factor that positively regulates HYR1 expression [17], exhibited enhanced susceptibility to phagocyte-mediated killing. The hyper-susceptibility to phagocyte killing of the bcr1 null mutant was fully complemented by autonomously expressed HYR1, but not other genes which encode GPI-proteins positively regulated by Bcr1p. Hence, HYR1 is a downstream gene of BCR1 in a phagocyte killing resistance pathway.

It is interesting that HL-60 derived neutrophils were able to inhibit the expression of HYR1 in wild-type *C. albicans* during the initial contact between the phagocytes and *Candida*. Thus, a dynamic interaction occurred between host phagocytes and *C. albicans*, in which the phagocytes mediated a delay in the expression of a phagocyte-resistance gene in the wild-type fungus. This is consistent with a previous finding that human neutrophils delayed the formation of *C. albicans* hyphae and the expression of hyphae co-expressed genes [18].

Resistance to phagocyte killing is a complex phenotype, likely attributable to multiple factors. Phagocytes can kill *Candida* extracellularly or intracellularly. Recently, *C. albicans* cell surface superoxide dismutases were characterized as virulence factors that help the fungi escape from killing by degrading host-derived highly reactive oxygen species [22]. Neutrophils typically attach to and spread over the surfaces of hyphal forms of fungi, as extended hyphae are too large for phagocytes to ingest completely. Since *C. albicans* expresses HYR1 in the hyphal form, it is possible that Hyr1p contributes to resistance to phagocyte killing by preventing surface contact to the phagocyte. Alternatively, Hyr1p might interfere with oxidative or non-oxidative killing mechanisms of phagocytes.

The in vitro phenotype of HYR1 overexpression was recapitulated in vivo. During murine disseminated infection, overexpression of HYR1 led to a significant increase, and suppression of HYR1 led to a significant decrease, in tissue fungal burden compared to the wild-type strain in organs with resident phagocytes. The lack of phenotype in the kidney likely reflects the fact that kidneys do not have resident phagocytes, and that neutrophil influx into the kidneys during lethal disseminated candidiasis does not begin until >24 hr of infection [15]. Nevertheless, vaccination with rHyr1p-N resulted in considerable protection against hematogenously disseminated candidiasis. The efficacy seen for the rHyr1p-N vaccine was greater than that previously seen in mice vaccinated with the rAls1p-N and rAls3p-N vaccines. Hence, rHyr1p-N is a promising vaccine candidate for disseminated candidiasis.

Our data also demonstrate the advantage of using a conditional overexpression/suppression approach to explore potential virulence functions of a given gene. Large-scale forward genetic approaches to explore virulence genes in vitro require functional screening assays, and are limited to screening for genes that are expressed while conducting the assay. When a gene is not expressed significantly in the wild-type strain under conditions used for the in vitro screening assay, forced overexpression of the gene still allows for detection of a gain-of-function phenomenon in the assay, as in the case of HYR1 during *Candida* blastospore growth. When a gene is strongly expressed, conditional suppression of the gene yields a loss-of-function phenotype in the same assay. Furthermore, when overexpression and suppression are used simultaneously, the phenotype can be amplified, as in the case of the effect of HYR1 on liver and spleen fungal burdens in vivo. The ability to detect a phenotype by comparing gene overexpression and suppression enables conditional gene expression to overcome the limitations of functional redundancy, which particularly plague forward genetic approaches when members of a gene family are being studied.

In summary, we used a conditional gene expression approach to identify Hyr1p as a surface expressed, virulence factor for *C. albicans*. HYR1 expression mediated resistance to neutrophil killing in vitro and increased tissue fungal burden in vivo. Finally, we demonstrated that HYR1 is a promising vaccine target which merits further development as a prophylactic strategy for disseminated candidiasis.

Materials and Methods

The above-described Results were obtained using the following materials and methods.

Strains and Culture Conditions

All strains used are listed in Table 1 and grown as previously described [8].

Conditional HYR1 Overexpression/Suppression Mutant Construction

To generate a conditional HYR1 expression strain, a HIS1-TR promoter cassette [8] was inserted in front of one allele of the HYR1 gene of strain THE4, yielding strain CAAH. The URA3 at the HIS1 locus in strain CAAH was looped out, generating CAAH-1. The second allele of HYR1 in CAAH-1 was disrupted by a recyclable URA3 cassette, generating strain CAAH-2, followed by looping out of URA3, yielding strain CAAH-3. A 3.9-kb Nhe I-Pst I fragment containing the URA3-IRO1 gene was inserted into its original locus on the CAAH-3 genome, yielding CAAH-31. Primers used are listed in Table 1.

Semi-Quantitative RT-PCR

The semi-quantitative RT-PCR to detect gene expression in vitro was described previously. Primers used to detect EFB1 expression were EFB1a and EFB1b; primers used to amplify HYR1 were HYR1 specific1 and HYR1 specific2 (Table 1). To study the impact of neutrophils on *C. albicans* HYR1 expression, $1 \times 10^6$ overnight cells of SC5314 grown in YPD were either co-cultured with $1 \times 10^7$ HL-60 derived neutrophils or cultured alone in RPMI 1640 plus 10% pooled human serum. Samples were taken at 30 min intervals for 3 hr until RNA was extracted, and semi-quantitative RT-PCR was performed.

Phagocyte Killing Assay

Human neutrophils were isolated, HL-60 cells were differentiated into neutrophils or macrophages, and the phagocyte killing assay was performed as previously described [8-10]. Briefly, phagocytes were incubated with fungi for 1 hr, and then sonicated and quantitatively cultured. Percent killing was calculated by dividing the number of fungal colonies after co-incubation with phagocytes by the number of fungal colonies incubated with media without phagocytes. Human neutrophils and HL-60 derived neutrophils or macrophages were tested at a 2:1 and 20:1 phagocyte:fungus ratio, respectively. For bcr1 and related mutants, the blastospores were pre-germinated for 40 min in RPMI plus 10% FBS at 37° C. before performing the assay.

Heterologous Expression of HYR1 in *C. glabrata* BG14

*C. glabrata* BG14 was transformed with either an HYR1 expression vector pGRB2.2-HYR1 or an empty control plasmid pGRB2.2 [11]. HYR1 coding sequence was amplified by CG-Hyr1-a and CG-Hyr1-b (Table 1) and was cloned into Xba Xho I sites of pGRB2.2 using In-Fusion™ 2.0 Dry-Down PCR Cloning Kit per manufacture's instruction (Clontech Laboratories, Mountain View, Calif.).

*C. albicans* HYR1 Expression During Hematogenous Infection

HYR1 expression by wild-type *C. albicans* SC5314 was examined during hematogenously disseminated candidiasis as described. Brains, livers, lungs, kidneys, and spleens of BALB/C mice were collected 6 and 24 hr post infection. Primers used are listed in Table 1. Reverse transcription was performed with RETROscript (Ambion, Tex.). For amplification of mouse G3PDH housekeeping gene, primers G3PDHF and G3PDHR were used. For detection of HYR1 and EFB1 of *C. albicans*, two rounds of PCR were performed. Round one used outer primer set (EFB1F and EFB1R for EFB1, or P2 and P5 for HYR1); round two used an aliquot (1 µl) of round one PCR product as a template. The inner primer sets were as follows: EFB1 nF and EFB1nR (for EFB1), or P2 and P4 (for HYR1). All PCR conditions were as follows: denaturing at 95° C., 2 min and amplification for 35 cycles at 94° C., 30 s (denaturing), 55° C., 30 s (annealing), and 72° C., 90 s (extension). For qRT-PCR, cDNA was prepared as above. Optimization of amplification efficiency and real-time RT-PCR SYBR green assays were carried out as described [12]. Constitutively expressed ACT1 was used as a control for all reactions. Calculations and statistical analyses were carried out as described in ABI PRISM 7000 Sequence Detection System User Bulletin 2 (Applied Biosystems, USA).

Tissue Fungal Burden

Mice were given water with or without DOX (2 mg/ml) dissolved in 5% sucrose solution throughout the period of the experiment starting from day −3 relative to infection [13], and were given food and water ad libitum. Tissue fungal burden was carried out as previously described [8] except that organs were removed 1 day post infection. All procedures involving mice were approved by the institutional animal use and care committee, following NIH guidelines.

rHyr1p-N Production rHyr1p-N (from amino acids 25-350 of Hyr1p) was produced in an *Escherichia coli* pQE-32 expression system (Qiagen), and the 6×His tagged protein was purified as described elsewhere, with the exception of using a HISPUR Cobalt resin (Thermo Scientific) affinity column. Endotoxin was removed from rHyr1p-N by using DETOXI-GEL Endotoxin Removing Columns (Thermo Scientific), and the endotoxin level was determined with *Limulus Amebocyte* Lysate endochrome (Charles River) per manufacturer's instruction. Using this procedure, endotoxin was reduced to <0.28 EU per dose used for vaccination.

Immunofluorescence Detection of Hyr1p Cellular Localization

Indirect immunofluorescence was performed using polyclonal anti-Hyr1p antisera generated by immunization of mice with rHyr1p-N (from amino acids 25-350). An inoculum of $1 \times 10^7$ blastospores of hyr1 null strain were incubated in RPMI 1640 for 90 min at 37° C. and pelleted twice to absorb the antiserum.

*C. albicans* blastospores ($1 \times 10^5$) were pre-germinated in RPMI 1640 for 90 min at 37° C. and transferred into a 4-well chamber slide (Nalge Nunc International Corp, Ill., USA). After incubation at 4° C. for 30 min, the cells were blocked with 300 µl of 1.5% goat serum, stained with polyclonal antiserum at a 1:100 dilution or PBS as a negative control, and then by fluorescein isothiocyanate-labeled goat anti-mouse IgG at 1:200. The cells were imaged by confocal scanning laser microscopy [15].

Immunization Protocol

All vaccinations were subcutaneous, at the base of the neck. Eight juvenile (10-12-week) C57BL/6 mice were vaccinated with 20 µg of affinity-purified rHyr1p-N in complete Freund's adjuvant and boosted in incomplete Freund's adjuvant (IFA) at 3 weeks. Eight additional juvenile mice received adjuvant alone mixed with the preparation produced from *E. coli* cells transformed with the empty plasmid. Fourteen days after the boost, mice were infected via the tail vein with $5 \times 10^5$ cells of wild-type *C. albicans* SC5314 [16].

The efficacy of rHyr1p-N in protecting against hematogenously disseminated candidiasis was also evaluated using alum (2% ALHYDROGEL; Brenntag Biosector), an adjuvant approved by the Food and Drug Administration (FDA) for use in humans. Additionally, to determine that rHyr1p-N was protective against other strains of *C. albicans*, we used another clinical isolate, strain 15563. For these experiments, 33 µg of affinity-purified rHyr1p-N was mixed with 0.1% ALHYDROGEL and administered to BALB/c mice as above on day 0, boosted on day 21, and then infected on day 35 with *C. albicans* through tail vein injection. For all vaccination experiments, survival of mice for 35 days after infection was used as an end point.

F(ab)'$_2$ Blocking Assay.

Pooled anti-Hyr1p or control serum was collected from 5 mice that were vaccinated either with rHyr1p-N or with the preparation produced from *E. coli* cells transformed with the empty plasmid. The total IgG from both sera was isolated using Nab Spin Kit (Thermo Scientific). The F(ab)'$_2$ fragments were purified with Pierce F(ab)'$_2$ Preparation Kit according to the manufacturer's instruction. *Candida* cells were opsonized on ice for 45 min with 5% normal mouse serum (Santa Cruz Biotechnology) or 5% normal mouse serum plus 5% F(ab)'$_2$ prepared from either rHyr1p-N vaccinated or control mice IgG before mixing with mouse neutrophils. Mouse neutrophil killing assay was described as above.

Statistical Analysis

Phagocyte mediated killing and tissue fungal burdens among different groups were compared by the Mann-Whitney U test for unpaired comparisons, as appropriate. The non-parametric Log Rank test was utilized to determine differences in survival times. P values of <0.05 were considered significant.

TABLE 1

Strains and oligonucleotides used in this study

| Strains | | |
|---|---|---|
| *Candida albicans* Strains | Genotype | Source |
| THE31 | ade2::hisG/ade2::hisG<br>HIS1/his1::dpl200<br>ura3-iro1::imm434/ura3-iro1::imm434::URA3-IRO1<br>ENO1/ENO1-tetR-ScHAP4AD-3XHA-ADE2 | [8] |
| CAAH | ade2::hisG/ade2::hisG<br>his1::URA3-dpl200/his1::dpl200<br>ura3-iro1::imm434/ura3-iro1::imm434<br>ENO1/ENO1-tetR-ScHAP4AD-3XHA-ADE2<br>HYR1/HIS1-pTR-HYR1 | [8] |

TABLE 1 -continued

Strains and oligonucleotides used in this study

| | | |
|---|---|---|
| CAAH-1 | ade2::hisG/ade2::hisG<br>his1::dpl200/his1::dpl200<br>ura3-iro1::imm434/ura3-iro1::imm434<br>ENO1/ENO1-tetR-ScHAP4AD-3XHA-ADE2<br>HYR1/HIS1-pTR-HYR1 | This study |
| CAAH-2 | ade2::hisG/ade2::hisG<br>his1::dpl200/his1::dpl200<br>ura3-iro1::imm434/ura3-iro1::imm434<br>ENO1/ENO1-tetR-ScHAP4AD-3XHA-ADE2<br>hyr1::URA3-dpl200/HIS1-pTR-HYR1 | This study |
| CAAH-3 | ade2::hisG/ade2::hisG<br>his1::dpl200/his1::dpl200<br>ura3-iro1::imm434/ura3-iro1::imm434<br>ENO1/ENO1-tetR-ScHAP4AD-3XHA-ADE2<br>hyr1::dpl200/HIS1-pTR-HYR1 | This study |
| CAAH-31 | ade2::hisG/ade2::hisG<br>his1::dpl200/his1::dpl200<br>ura3-iro1::imm434/ura3-iro1::imm934::URA3-IRO1<br>ENO1/ENO1-tetR-ScHAP4AD-3XHA-ADE2<br>hyr1::dpl200/HIS1-pTR-HYR1 | This study |
| DAY185 | ura3-iro1::imm434/ura3-iro1::imm434<br>his1::hisG::pHIS1/his1::hisG<br>arg4::hisG::ARG4-URA3/arg4::hisG | [17] |
| CJN702 | ura3-iro1::imm434/ura3-iro1::imm434<br>his1::hisG::pHIS1/his1::hisG<br>arg4::hisG/arg4::hisG<br>bcr1::ARG4/bcr1::URA3 | [17] |
| CJN698 | ura3-iro1::imm434/ura3-iro1::imm434<br>his1::hisG::pHIS1-BCR1/his1::hisG<br>arg4::hisG/arg4::hisG<br>bcr1::ARG4/bcr1::URA3 | [17] |
| CJN1144 | ura3-iro1::imm434/ura3-iro1::imm434<br>his1::hisG::pHIS1-$P_{TEF1}$-ALS1-$t_{TEF1}$/his1::hisG<br>arg4::hisG/arg4::hisG<br>bcr1::ARG4/bcr1::URA3 | [17] |
| CJN1153 | ura3-iro1::imm434/ura3-iro1::imm434<br>his1::hisG::pHIS1-$P_{TEF1}$-ALS3-$t_{TEF1}$/his1::hisG<br>arg4::hisG/arg4::hisG<br>bcr1::ARG4/bcr1::URA3 | [17] |
| CJN1222 | ura3-iro1::imm434/ura3-iro1::imm434<br>his1::hisG::pHIS1-$P_{TEF1}$-HWP1-$t_{TEF1}$/his1::hisG<br>arg4::hisG/arg4::hisG<br>bcr1::ARG4/bcr1::URA3 | [17] |
| CJN1259 | ura3-iro1::imm434/ura3-iro1::imm434<br>his1::hisG::pHIS1-$P_{TEF1}$-HYR1-$t_{TEF1}$/his1::hisG<br>arg4::hisG/arg4::hisG<br>bcr1::ARG4/bcr1::URA3 | [17] |
| CJN1276 | ura3-iro1::imm434/ura3-iro1::imm434<br>his1::hisG::pHIS1-$P_{TEF1}$-RBT51-$t_{TEF1}$/his1::hisG<br>arg4::hisG/arg4::hisG<br>bcr1::ARG4/bcr1::URA3 | [17] |
| CJN1281 | ura3-iro1::imm434/ura3-iro1::imm434<br>his1::hisG::pHIS1-$P_{TEF1}$-CHT2-$t_{TEF1}$/his1::hisG<br>arg4::hisG/arg4::hisG<br>bcr1::ARG4/bcr1::URA3 | [17] |
| CJN1288 | ura3-iro1::imm434/ura3-iro1::imm434<br>his1::hisG::pHIS1-$P_{TEF1}$-ECE1-$t_{TEF1}$/his1::hisG<br>arg4::hisG/arg4::hisG<br>bcr1::ARG4/bcr1::URA3 | [17] |
| Candida glabrata strain BG14 | ura3Δ(-85 + 932)::Tn903NeoR | [17] |

TABLE 1 -continued

Strains and oligonucleotides used in this study

Oligonucleotides

Oligonucleotides used for making and confirming HYR1 conditional overexpression/suppression strain

| | |
|---|---|
| P1 | 5'-ACTTGGCACCAGGAACAAC (SEQ ID NO. 3) |
| P2 | 5'-ACAGCTTTATCTCAGAAAAACTAGTAATAACAACATGAAAGTGGTATCA (SEQ ID NO. 4) |
| P3 | 5'-CGACAAACACAACGGCACATTCTGGTTTCAACAAACTGGAATACTTTG (SEQ ID NO. 5) |
| P4 | 5'-AGCAGTAACACAACCAGTACCT (SEQ ID NO. 6) |
| PH1 | 5'-GTCGTCGCTGTGTTTGTC (SEQ ID NO. 7) |
| PH2 | 5'-CGTTGGAGAAGGTAATTGTGA (SEQ ID NO. 8) |
| P5 | 5'-CAGCATGAACAATCAAAGACGA (SEQ ID NO. 9) |
| P6 | 5'-CAAAGTATTCCAGTTTGTTGAAACC (SEQ ID NO. 10) |

Oligonucleotides used for detecting in vitro expression

| | |
|---|---|
| HYR1 specific1 | 5'-CGTCAACCTGACTGTTACATC (SEQ ID NO. 11) |
| HYR1 specific2 | 5'-TCTACGGTGGTATGTGGAAC (SEQ ID NO. 12) |
| EFB1a | 5'-ATTGAACGAATTCTTGGCTGAC (SEQ ID NO. 13) |
| EFB1b | 5'-CATCTTCTTCAACAGCAGCTTG (SEQ ID NO. 14) |

Oligonucleotides used for for in vivo expression

| | |
|---|---|
| EFB1F | 5'-CACAAACCAATACATAATG (SEQ ID NO. 15) |
| EFB1R | 5'-GTAGACAGTGACATCAGC (SEQ ID NO. 16) |
| EFB1nF | 5'-TCAGATTTCTCTAAAGTCG (SEQ ID NO. 17) |
| EFB1nR | 5'-TGACATCAGCTTGAGTGG (SEQ ID NO. 18) |
| G3PDHF | 5'-GTCTTCACCACCATGGAGAAGG (SEQ ID NO. 19) |
| G3PDHR | 5'-TCGCTGTTGAAGTCAGAGGAGA (SEQ ID NO. 20) |

Oligonucleotides used for confirming URA3-IRO1 in its original locus

| | |
|---|---|
| URA3 Conf1 | 5'-TGCTGGTTGGAATGCTTATTTG (SEQ ID NO. 21) |
| URA3 Conf2 | 5'-TGCAAATTCTGCTACTGGAGTT (SEQ ID NO. 22) |

Oligonucleotides used for HYR1 expression construct in C. glabrata

| | |
|---|---|
| CG-Hyr1-a | 5'-ATATAAAACATCTAGATGAAAGTGGTATCAAACTTTATATTC (SEQ ID NO. 23) |
| CG-Hyr1-b | 5'-GGGTTGTGTTCTCGATCACATGAATAAAACAACCATG (SEQ ID NO. 24) |

Example II rHyr1p-N is a Vaccine Against Disseminated Candidiasis

Background:

We have found that overexpression of HYR1 by *Candida albicans* mediates resistance to neutrophil killing in vitro. We sought to determine the impact of HYR1 overexpression on tissue fungal burden in vivo during infection, and to define the potential for vaccination with rHyr1p-N to protect against disseminated candidiasis in mice.

Methods:

Mice were infected via the tail-vein with HYR1 overexpression/suppression or wild-type *C. albicans*. Livers and spleens were harvested 1 day post infection and the expression levels of HYR1 and tissue fungal burden were determined by qRT-PCR and quantitative culturing, respectively. For vaccination, rHyr1p-N was produced in *E. coli* pQE-32 expression system and purified per the manufactures' instruction (Qiagen). Mice were vaccinated with 20 μg of rHyr1p-N in complete Freund's adjuvant (CFA), boosted in incomplete Freund's adjuvant (IFA) at 3 weeks, and infected with *C. albicans* strain SC5314 two weeks post the boost. Control mice received adjuvant plus cell extract from *E. coli* transformed with empty plasmid.

Results:

Overexpression of HYR1 significantly increased fungal burden in both livers and spleens compared to control strain. Suppression of HYR1 significantly reduced fungal burden in both livers and spleens compared to control strain. The relative level of expression of HYR1 was 2.5 and 0.8 in livers infected with overexpression or suppression strain versus the control strain, respectively. The rHyr1p-N vaccine resulted in 62.5% long-term survival of infected mice, versos 0% survival in control mice.

Conclusions:

HYR1 expression affects the ability of *C. albicans* to infect tissues in vivo. Furthermore, vaccination with rHyr1p-N markedly protected mice from disseminated candidiasis. The rHyr1p-N vaccine is useful to prevent disseminated candidiasis.

REFERENCES

1. Spellberg B J, Filler S G, and Edwards J E, Jr. Current treatment strategies for disseminated candidiasis. Clin Infect Dis. 2006; 42:244-251
2. Del Poeta M. Role of Phagocytosis in the Virulence of *Cryptococcus neoformans*. Eukaryot Cell 2004; 3:1067-1075
3. Koh A Y, Kohler J R, Coggshall K T, Van Rooijen N and Pier G B. Mucosal damage and neutropenia are required for *Candida albicans* dissemination. PLoS Pathog. 2008; 4:DOI:10.1371/journal.ppat.0040035.
4. Gulay Z, Imir T. Anti-candidial activity of natural killer (NK) and lymphokine activated killer (LAK) lymphocytes in vitro. Immunobiology 1996; 195:220-230
5. Stone H H. Studies in the pathogenesis, diagnosis, and treatment of *Candida* sepsis in children. J Pediatr Surg. 1974; 9:127-133
6. Richard M, Ibata-Ombetta S, Dromer F, Bordon-Pallier F, Jouault T and Gaillardin C. Complete glycosylphosphatidylinositol anchors are required in *Candida albicans* for full morphogenesis, virulence and resistance to macrophages. Mol. Microbiol. 2002; 44
7. Bailey D A, Feldmann P J, Bovey M, Gow N A and Brown A J. The *Candida albicans* HYR1 gene, which is activated in response to hyphal development, belongs to a gene family encoding yeast cell wall proteins. J Bacteriol. 1996; 178:5353-5360
8. Fu Y, Luo G., Spellberg B J, Edwards J E, Jr, and Ibrahim A S. Gene overexpression/suppression analysis of candidate virulence factors of *Candida albicans*. Eukaryot Cell. 2008; 7:483-492
9. Nusing R, Goerig M, Habenicht A J and Ullrich V. Selective eicosanoid formation during HL-60 macrophage differentiation. Regulation of thromboxane synthase. Eur J Biochem 1993; 212:371-376
10. Spellberg B J, Collins M, French S W, Edwards J E, Jr., Fu Y and Ibrahim A S. A phagocytic cell line markedly improves survival of infected neutropenic mice. J Leukoc Biol 2005; 78:338-344
11. Eiden-Plach A, Zagorc T, Heintel T, Carius Y, Breinig F. Viral preprotoxin signal sequence allows efficient secretion of green fluorescent protein by *Candida glabrata, Pichia pastoris, Saccharomyces cerevsiae*, and *Schizosaccharomyces pombe*. Appl. Environ. Microbiol 2004; 70:961-966
12. Avrova A O, Venter E, Birch P R and Whisson S C. Profiling and quantifying differential gene transcription in *Phytophthora infestans* prior to and during the early stages of potato infection. Fungal Genetics & Biology 2003; 40:4-14
13. Saville S P, Lazzell A L, Monteagudo C and Lopez-Ribot J L. Engineered control of cell morphology in vivo reveals distinct roles for yeast and filamentous forms of *Candida albicans* during infection. Eukaryot Cell 2003; 2:1053-1060.
14. Spellberg B, Ibrahim A S, Yeaman M R, et al. The antifungal vaccine derived from the recombinant N terminus of Als3p protects mice against the bacterium *Staphylococcus aureus*. Infect Immun. 2008; 76:4574-4580
15. Fu Y, Ibrahim A S, Sheppard D C, Chen Y C, French S W and Cutler J Eea. *Candida albicans* Als1p: an adhesin that is a downstream effector of the EFG1 filamentation pathway. Mol Microbiol 2002; 44:61-72
16. Ibrahim A S, Spellberg B J, Avenissian V, Fu Y, Filler S G and Edwards J E J. Vaccination with rAls1p-N improves survival during murine disseminated candidiasis by enhancing cell-mediated, not humoral, immunity. Infect Immun 2005; 73:999-1005
17. Nobile C J, Andes D R, Nett J E, et al. Critical role of Bcr1-dependent adhesins in *C. albicans* biofilm formation in vitro and in vivo. PLoS Pathog. 2006; 2:e63
18. Fradin C, De Groot P, MacCallum D, et al. Granulocytes govern the transcriptional response, morphology and proliferation of *Candida* albicans in human blood. Molecular Microbiology 2005; 56:397-415
19. Castano I, Pan S J, Zupancic M, Hennequin C, Dujon B and Cormack B P. Telomere length control and transcriptional regulation of subtelomeric adhesins in *Candida glabrata*. Mol Microbiol 2005; 55:1246-1258
20. Schofield D A, Westwater C, Warner T, Nicholas P J, Paulling E E and Balish E. Hydrolytic gene expression during oroesophageal and gastric candidiasis in immunocompetent and immunodeficient gnotobiotic mice. J Infect Dis 2003; 188:591-599
21. Kumamoto C A, Vinces M D. Contributions of hyphae and hypha-co-regulated genes to *Candida albicans* virulence. Cell Microbiol. 2005; 7:1546-1554
22. Frohner I E, Bourgeois C, Yatsyk K, Majer O and Kuchler K. *Candida albicans* cell surface superoxide dismutases degrade host-derived reactive oxygen species to escape innate immune surveillance. Mol Microbiol 2009; 71:240-252

What is claimed is:

1. An immunogenic composition comprising an isolated polypeptide optionally fused to a heterologous fusion sequence and a pharmaceutically acceptable carrier, wherein the amino acid sequence of said polypeptide consists of the amino acid sequence of SEQ ID NO: 2.

2. The immunogenic composition of claim 1, further comprising an adjuvant.

3. The immunogenic composition of claim 1, wherein the polypeptide is fused to the heterologous fusion sequence.

4. The immunogenic composition of claim 3, wherein the heterologous fusion sequence is a heterologous leader sequence, a tag, or a linker sequence.

5. The immunogenic composition of claim 4, wherein the tag is a histidine tag.

6. The immunogenic composition of claim 4, wherein the polypeptide is obtained from a transformed cell.

7. The immunogenic composition of claim 6, wherein the transformed cell is a transformed *Saccharomyces cerevisiae* cell.

8. The immunogenic composition of claim 4, wherein the composition is a vaccine composition for immunization against *Candida albicans* and the polypeptide is purified.

9. A method of immunizing a mammalian host against *Candida albicans* comprising administering to said host an immunogenically effective amount of the vaccine composition of claim 8.

10. The method of claim 9, wherein the vaccine composition further comprises an adjuvant.

* * * * *

SEQUENCE LISTING

```
<160> NUMBER OF SEQ ID NOS: 24

<210> SEQ ID NO 1
<211> LENGTH: 937
<212> TYPE: PRT
<213> ORGANISM: Candida albicans

<400> SEQUENCE: 1

Met Lys Val Val Ser Asn Phe Ile Phe Thr Ile Leu Leu Thr Leu Asn
1               5                   10                  15
```

```
Leu Ser Ala Ala Leu Glu Val Val Thr Ser Arg Ile Asp Arg Gly Gly
            20                  25                  30

Ile Gln Gly Phe His Gly Asp Val Lys Val His Ser Gly Ala Thr Trp
        35                  40                  45

Ala Ile Leu Gly Thr Thr Leu Cys Ser Phe Phe Gly Gly Leu Glu Val
    50                  55                  60

Glu Lys Gly Ala Ser Leu Phe Ile Lys Ser Asp Asn Gly Pro Val Leu
65                  70                  75                  80

Ala Leu Asn Val Ala Leu Ser Thr Leu Val Arg Pro Val Ile Asn Asn
                85                  90                  95

Gly Val Ile Ser Leu Asn Ser Lys Ser Ser Thr Ser Phe Ser Asn Phe
                100                 105                 110

Asp Ile Gly Gly Ser Ser Phe Thr Asn Asn Gly Glu Ile Tyr Leu Asp
                115                 120                 125

Ser Ser Gly Leu Val Lys Ser Thr Ala Tyr Leu Tyr Ala Arg Glu Trp
130                 135                 140

Thr Asn Asn Gly Leu Ile Val Ala Tyr Gln Asn Gln Lys Ala Ala Gly
145                 150                 155                 160

Asn Ile Ala Phe Gly Thr Ala Tyr Gln Thr Ile Thr Asn Asn Gly Gln
                165                 170                 175

Ile Cys Leu Arg His Gln Asp Phe Val Pro Ala Thr Lys Ile Lys Gly
                180                 185                 190

Thr Gly Cys Val Thr Ala Asp Glu Asp Thr Trp Ile Lys Leu Gly Asn
                195                 200                 205

Thr Ile Leu Ser Val Glu Pro Thr His Asn Phe Tyr Leu Lys Asp Ser
210                 215                 220

Lys Ser Ser Leu Ile Val His Ala Val Ser Ser Asn Gln Thr Phe Thr
225                 230                 235                 240

Val His Gly Phe Gly Asn Gly Asn Lys Leu Gly Leu Thr Leu Pro Leu
                245                 250                 255

Thr Gly Asn Arg Asp His Phe Arg Phe Glu Tyr Tyr Pro Asp Thr Gly
                260                 265                 270

Ile Leu Gln Leu Arg Ala Asp Ala Leu Pro Gln Tyr Phe Lys Ile Gly
                275                 280                 285

Lys Gly Tyr Asp Ser Lys Leu Phe Arg Ile Val Asn Ser Arg Gly Leu
                290                 295                 300

Lys Asn Ala Val Thr Tyr Asp Gly Pro Val Pro Asn Asn Glu Ile Pro
305                 310                 315                 320

Ala Val Cys Leu Ile Pro Cys Thr Asn Gly Pro Ser Ala Pro Glu Ser
                325                 330                 335

Glu Ser Asp Leu Asn Thr Pro Thr Thr Ser Ser Ile Glu Thr Ser Ser
                340                 345                 350

Tyr Ser Ser Ala Ala Thr Glu Ser Ser Val Val Ser Glu Ser Ser Ser
                355                 360                 365

Ala Val Asp Ser Leu Thr Ser Ser Ser Leu Ser Ser Lys Ser Glu Ser
                370                 375                 380

Ser Asp Val Val Ser Thr Thr Asn Ile Glu Ser Ser Ser Thr Ala
385                 390                 395                 400

Ile Glu Thr Thr Met Asn Ser Glu Ser Ser Thr Asp Ala Gly Ser Ser
                405                 410                 415

Ser Ile Ser Gln Ser Glu Ser Ser Ser Thr Ala Ile Thr Ser Ser Ser
                420                 425                 430

Glu Thr Ser Ser Ser Glu Ser Met Ser Ala Ser Ser Thr Thr Ala Ser
```

-continued

```
                435                 440                 445
Asn Thr Ser Ile Glu Thr Asp Ser Gly Ile Val Ser Gln Ser Glu Ser
450                 455                 460
Ser Ser Asn Ala Leu Ser Ser Thr Glu Gln Ser Ile Thr Ser Ser Pro
465                 470                 475                 480
Gly Gln Ser Thr Ile Tyr Val Asn Ser Thr Val Thr Ser Thr Ile Thr
                485                 490                 495
Ser Cys Asp Glu Asn Lys Cys Thr Glu Asp Val Val Thr Ile Phe Thr
                500                 505                 510
Thr Val Pro Cys Ser Thr Asp Cys Val Pro Thr Thr Gly Asp Ile Pro
                515                 520                 525
Met Ser Thr Ser Tyr Thr Gln Arg Thr Val Thr Ser Thr Ile Thr Asn
                530                 535                 540
Cys Asp Glu Val Ser Cys Ser Gln Asp Val Val Thr Tyr Thr Thr Asn
545                 550                 555                 560
Val Pro His Thr Thr Val Asp Ala Thr Thr Thr Thr Thr Thr Ser Thr
                565                 570                 575
Gly Gly Asp Asn Ser Thr Gly Gly Asn Glu Ser Gly Ser Asn His Gly
                580                 585                 590
Pro Gly Asn Gly Ser Thr Glu Gly Ser Gly Asn Gly Ser Gly Ala Gly
                595                 600                 605
Ser Asn Glu Gly Ser Gln Ser Gly Pro Asn Asn Gly Ser Gly Ser Gly
610                 615                 620
Ser Glu Gly Gly Ser Asn Asn Gly Ser Gly Ser Asp Ser Gly Ser Asn
625                 630                 635                 640
Asn Gly Ser Gly Ser Gly Ser Asn Asn Gly Ser Gly Ser Gly Ser Thr
                645                 650                 655
Glu Gly Ser Glu Gly Gly Ser Gly Ser Asn Glu Gly Ser Gln Ser Gly
                660                 665                 670
Ser Gly Ser Gln Pro Gly Pro Asn Glu Gly Ser Glu Gly Gly Ser Gly
                675                 680                 685
Ser Asn Glu Gly Ser Asn His Gly Ser Asn Glu Gly Ser Gly Ser Gly
                690                 695                 700
Ser Gly Ser Gly Ser Asn Asn Gly Ser Gly Ser Gly Ser Gln Ser Gly
705                 710                 715                 720
Ser Gly Ser Gly Ser Gln Ser Gly Ser Glu Gly Ser Asn Ser Gly
                725                 730                 735
Ser Asn Glu Gly Ser Asn Pro Gly Ala Gly Asn Gly Ser Asn Glu Gly
                740                 745                 750
Ser Gly Gln Gly Ser Gly Asn Gly Ser Glu Ala Gly Ser Gly Gln Gly
                755                 760                 765
Ser Gly Pro Asn Asn Gly Ser Gly Ser His Asn Asp Gly Ser Gly
                770                 775                 780
Ser Gly Ser Asn Gln Gly Ser Asn Pro Gly Ala Gly Ser Gly Ser Gly
785                 790                 795                 800
Ser Glu Ser Gly Ser Lys Ala Gly Ser His Ser Gly Ser Asn Glu Gly
                805                 810                 815
Ala Lys Thr Asp Ser Ile Glu Gly Phe His Thr Glu Ser Lys Pro Gly
                820                 825                 830
Phe Asn Thr Gly Ala His Thr Asp Ala Thr Val Thr Gly Asn Ser Val
                835                 840                 845
Ala Asn Pro Val Thr Thr Ser Thr Glu Ser Asp Thr Thr Ile Ser Val
850                 855                 860
```

```
Thr Val Ser Ile Thr Ser Tyr Met Thr Gly Phe Asp Gly Lys Pro Lys
865                 870                 875                 880

Pro Phe Thr Thr Val Asp Val Ile Pro Val Pro His Ser Met Pro Ser
                885                 890                 895

Asn Thr Asp Ser Ser Ser Val Pro Thr Ile Asp Thr Asn Glu
            900                 905                 910

Asn Gly Ser Ser Ile Val Thr Gly Gly Lys Ser Ile Leu Phe Gly Leu
            915                 920                 925

Ile Val Ser Met Val Val Leu Phe Met
            930                 935

<210> SEQ ID NO 2
<211> LENGTH: 326
<212> TYPE: PRT
<213> ORGANISM: Candida albicans

<400> SEQUENCE: 2

Thr Ser Arg Ile Asp Arg Gly Gly Ile Gln Gly Phe His Gly Asp Val
1               5                   10                  15

Lys Val His Ser Gly Ala Thr Trp Ala Ile Leu Gly Thr Thr Leu Cys
                20                  25                  30

Ser Phe Phe Gly Gly Leu Glu Val Glu Lys Gly Ala Ser Leu Phe Ile
            35                  40                  45

Lys Ser Asp Asn Gly Pro Val Leu Ala Leu Asn Val Ala Leu Ser Thr
50                  55                  60

Leu Val Arg Pro Val Ile Asn Asn Gly Val Ile Ser Leu Asn Ser Lys
65                  70                  75                  80

Ser Ser Thr Ser Phe Ser Asn Phe Asp Ile Gly Gly Ser Ser Phe Thr
                85                  90                  95

Asn Asn Gly Glu Ile Tyr Leu Ala Ser Ser Gly Leu Val Lys Ser Thr
            100                 105                 110

Ala Tyr Leu Tyr Ala Arg Glu Trp Thr Asn Asn Gly Leu Ile Val Ala
            115                 120                 125

Tyr Gln Asn Gln Lys Ala Ala Gly Asn Ile Ala Phe Gly Thr Ala Tyr
            130                 135                 140

Gln Thr Ile Thr Asn Asn Gly Gln Ile Cys Leu Arg His Gln Asp Phe
145                 150                 155                 160

Val Pro Ala Thr Lys Ile Lys Gly Thr Gly Cys Val Thr Ala Asp Glu
                165                 170                 175

Asp Thr Trp Ile Lys Leu Gly Asn Thr Ile Leu Ser Val Glu Pro Thr
            180                 185                 190

His Asn Phe Tyr Leu Lys Asp Ser Lys Ser Ser Leu Ile Val His Ala
            195                 200                 205

Val Ser Ser Asn Gln Thr Phe Thr Val His Gly Phe Gly Asn Gly Asn
210                 215                 220

Lys Leu Gly Leu Thr Leu Pro Leu Thr Gly Asn Arg Asp His Phe Arg
225                 230                 235                 240

Phe Glu Tyr Tyr Pro Asp Thr Gly Ile Leu Gln Leu Arg Ala Ala Ala
                245                 250                 255

Leu Pro Gln Tyr Phe Lys Ile Gly Lys Gly Tyr Asp Ser Lys Leu Phe
            260                 265                 270

Arg Ile Val Asn Ser Arg Gly Leu Lys Asn Ala Val Thr Tyr Asp Gly
            275                 280                 285

Pro Val Pro Asn Asn Glu Ile Pro Ala Val Cys Leu Ile Pro Cys Thr
            290                 295                 300
```

Asn Gly Pro Ser Ala Pro Glu Ser Glu Ser Asp Leu Asn Thr Pro Thr
305                 310                 315                 320

Thr Ser Ser Ile Glu Thr
            325

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
acttggcacc aggaacaac                                              19

<210> SEQ ID NO 4
<211> LENGTH: 49
<212> TYPE: DNA
<213> ORGANISM: Artificial Sequence
<220> FEATURE:
<223> OTHER INFORMATION: Synthetic Construct

<400> SEQUENCE: 4
acagctttat ctcagaaaaa ctagtaataa caacatgaaa gtggtatca              49

<210> SEQ ID NO 5
<211> LENGTH: 48
<212> TYPE: DNA
<213> ORGANISM: Artificial Sequence
<220> FEATURE:
<223> OTHER INFORMATION: Synthetic Construct

<400> SEQUENCE: 5
cgacaaacac aacggcacat tctggtttca acaaactgga atactttg               48

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
agcagtaaca caaccagtac ct                                           22

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct

<400> SEQUENCE: 7
gtcgtcgctg tgtttgtc                                                18

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
cgttggagaa ggtaattgtg a                                            21

<210> SEQ ID NO 9

```
<211> LENGTH: 22
<212> TYPE: DNA
<213> ORGANISM: Artificial Sequence
<220> FEATURE:
<223> OTHER INFORMATION: Synthetic Construct

<400> SEQUENCE: 9
cagcatgaac aatcaaagac ga                                              22

<210> SEQ ID NO 10
<211> LENGTH: 25
<212> TYPE: DNA
<213> ORGANISM: Artificial Sequence
<220> FEATURE:
<223> OTHER INFORMATION: Synthetic Construct

<400> SEQUENCE: 10
caaagtattc cagtttgttg aaacc                                           25

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
cgtcaacctg actgttacat c                                               21

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
tctacggtgg tatgtggaac                                                 20

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13
attgaacgaa ttcttggctg ac                                              22

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct

<400> SEQUENCE: 14
catcttcttc aacagcagct tg                                              22

<210> SEQ ID NO 15
<211> LENGTH: 19
<212> TYPE: DNA
<213> ORGANISM: Artificial Sequence
<220> FEATURE:
<223> OTHER INFORMATION: Synthetic Construct

<400> SEQUENCE: 15
```

```
cacaaaccaa tacataatg                                                  19

<210> SEQ ID NO 16
<211> LENGTH: 18
<212> TYPE: DNA
<213> ORGANISM: Artificial Sequence
<220> FEATURE:
<223> OTHER INFORMATION: Synthetic Construct

<400> SEQUENCE: 16
gtagacagtg acatcagc                                                   18

<210> SEQ ID NO 17
<211> LENGTH: 19
<212> TYPE: DNA
<213> ORGANISM: Artificial Sequence
<220> FEATURE:
<223> OTHER INFORMATION: Synthetic Construct

<400> SEQUENCE: 17
tcagatttct ctaaagtcg                                                  19

<210> SEQ ID NO 18
<211> LENGTH: 18
<212> TYPE: DNA
<213> ORGANISM: Artificial Sequence
<220> FEATURE:
<223> OTHER INFORMATION: Synthetic Construct

<400> SEQUENCE: 18
tgacatcagc ttgagtgg                                                   18

<210> SEQ ID NO 19
<211> LENGTH: 22
<212> TYPE: DNA
<213> ORGANISM: Artificial Sequence
<220> FEATURE:
<223> OTHER INFORMATION: Synthetic Construct

<400> SEQUENCE: 19
gtcttcacca ccatggagaa gg                                              22

<210> SEQ ID NO 20
<211> LENGTH: 22
<212> TYPE: DNA
<213> ORGANISM: Artificial Sequence
<220> FEATURE:
<223> OTHER INFORMATION: Synthetic Construct

<400> SEQUENCE: 20
tcgctgttga agtcagagga ga                                              22

<210> SEQ ID NO 21
<211> LENGTH: 22
<212> TYPE: DNA
<213> ORGANISM: Artificial Sequence
<220> FEATURE:
<223> OTHER INFORMATION: Synthetic Construct

<400> SEQUENCE: 21
tgctggttgg aatgcttatt tg                                              22

<210> SEQ ID NO 22
<211> LENGTH: 22
<212> TYPE: DNA
<213> ORGANISM: Artificial Sequence
<220> FEATURE:
```

```
<223> OTHER INFORMATION: Synthetic Construct

<400> SEQUENCE: 22
tgcaaattct gctactggag tt                                              22

<210> SEQ ID NO 23
<211> LENGTH: 42
<212> TYPE: DNA
<213> ORGANISM: Artificial Sequence
<220> FEATURE:
<223> OTHER INFORMATION: Synthetic Construct

<400> SEQUENCE: 23
atataaaaca tctagatgaa agtggtatca aactttatat tc                        42

<210> SEQ ID NO 24
<211> LENGTH: 37
<212> TYPE: DNA
<213> ORGANISM: Artificial Sequence
<220> FEATURE:
<223> OTHER INFORMATION: Synthetic Construct

<400> SEQUENCE: 24
gggttgtgtt ctcgatcaca tgaataaaac aaccatg                              37
```